United States Patent [19]

Albrecht et al.

[11] Patent Number: 4,804,399

[45] Date of Patent: Feb. 14, 1989

[54] LIQUID PESTICIDAL COMPOSITIONS IN THE FORM OF SUSPENSION CONCENTRATES

[75] Inventors: Konrad Albrecht, Kelkheim; Gerhard Frisch, Wehrheim, both of Fed. Rep. of Germany

[73] Assignee: Hoechst Aktiengesellschaft, Frankfurt am Main, Fed. Rep. of Germany

[21] Appl. No.: 818,891

[22] Filed: Jan. 14, 1986

[30] Foreign Application Priority Data

Nov. 5, 1982 [DE] Fed. Rep. of Germany ....... 3240862

[51] Int. Cl.$^4$ ............................................. A01N 25/30
[52] U.S. Cl. .................... 71/93; 71/DIG. 5; 514/975
[58] Field of Search .............. 71/DIG. 5, 93; 514/975

[56] References Cited

U.S. PATENT DOCUMENTS

| | | | |
|---|---|---|---|
| 3,873,689 | 3/1975 | Freusch et al. | 71/DIG. 1 |
| 3,888,828 | 6/1975 | Grossmann et al. | 71/79 |
| 3,920,442 | 11/1975 | Albert et al. | 71/DIG. 1 |
| 3,948,636 | 4/1976 | Marks | 71/DIG. 1 |
| 4,155,741 | 5/1979 | Scher et al. | 71/DIG. 1 |

OTHER PUBLICATIONS

Farm Chemicals Handbook 1976, p. D81, Meister Pub. Co., 1976.
"The Pesticide Manual", pp. 23, 89, 233, 271.

*Primary Examiner*—Catherine L. Mills
*Attorney, Agent, or Firm*—Curtis, Morris & Safford

[57] ABSTRACT

Subject of the invention are liquid pesticidal compositions in the form of aqueous suspension concentrates, which in addition to the active substance or mixture of active substances contain an alkali metal salt of sulfosuccinic acid semiester prepared by reaction of a polyglycol ether of a condensation product of ($C_8$–$C_{12}$)-alkylphenol and formaldehyde with maleic anhydride and an alkali metal sulfite, in combination with a mixture of an alkali metal salt of a ligninsulfonic acid and identical parts of a swelling alkaline earth metal silicate. These suspension concentrates have an advantageous stability to storage.

11 Claims, No Drawings

LIQUID PESTICIDAL COMPOSITIONS IN THE FORM OF SUSPENSION CONCENTRATES

This application is a continuation of application Ser. No. 547,747, filed Nov. 1, 1983, now abandoned.

The present invention relates to liquid formulations of pesticides in the form of suspension concentrates.

Generally, pesticidal substances are applied in the form of emulsifiable conentrates, wettable powders or suspension concentrates. Active substances scarcely soluble in industrial grade solvents are generally applied in the form of wettable powders. However, expensive grinding and filtering apparatus are often also expensive carriers are required for the manufacture of these formulations. Wettable powders have moreover the disadvantage of giving off dust on handling, so that the dosage thereof is difficult. There is the risk for the user to be contaminated by such dust formulations and thus to become impaired. Spraying liquors prepared from wettable powders tend to become inhomogeneous because the particles of active substance and solids sediment relatively rapidly.

In contrast to wettable powders, aqueous suspensions do not have these disadvantages. The apparatus expenditure is relatively low because filtering devices are not required for the manufacture thereof. It is however difficult to develop suspension concentrates stable to storage and suitable for application in practice. While emulsifiable concentrates and wettable powders are monophase systems, aqueous suspension concentrates of solid active substances are two-phase systems (solid/liquid), which generally are unstable and tend to separation; this tendency increasing with increasing storage time and storage temperature. In practice, however, suspension concentrates must be stable to storage for more than 2 years, and they must furthermore remain pourable; solidification of suspensions and/or irreversible sediment formation must be excluded.

Although theories on the conditions for the formation of stable suspensions exist, it is impossible to predetermine directly optimum formulation additives due to the multitude of criteria to be taken into consideration. Thus, for example, it does not suffice in practice to test the suspension behavior of one single production batch, because even a slight alteration of the proportion of by-components in the individual batches of active substance may adversely affect the stability of the dispersions to a decisive extent.

Numerous compositions of suspension concentrates are known from the literature. When known pesticides, for example triphenyl tin compounds, ureas such as diuron or linuron, triazines such as simazine, atrazine, or active substances such as carbendazime, chlorotoluron, maneb, mancozeb or endosulfan, are formulated with the aid of partially hydrolyzed polyvinyl acetates as described in U.S. Pat. No. 4,071,617, optimum formulations are not obtained, because these formulation additives cause the formation of viscous sediments which cannot be redispersed. The same effect is observed when employing nonionic emulsifiers, vegetable gums and anionic surface-active agents for the formulation, for example according to U.S. Pat. No. 3,948,636 or British Pat. No. 1,480,110.

Nonionic emulsifiers which contain polyglycol ether groups often cause the formation of crystals, for example in the case of the relatively scarcely soluble pesticide diuron. The use of high polymer polyglycol ethers besides dispersing agents, even with addition of silicic acid (see German Offenlegungsschriften Nos. 2,547,968 and 2,651,046) gives dispersions which on storage precipitate irreversible bottom sediments. When pesticides are formulated with the use of polycarboxylated vinyl polymers, for example polymethacrylates (U.S. Pat. No. 3,060,084), viscous sediments likewise precipitate very often on storage. Suspension concentrates which thickens at 40°-50° C. or which forms viscous sediments and therefore are unfit for use and not at all stable to storage are obtained, furthermore, when formulating pesticides such as those indicated above by means of a polycarboxylated vinyl polymer according to German Offenlegungsschrift No. 2,651,046.

Dispersions containing ligninsulfonates as formulation auxiliary according to U.S. Pat. No. 3,157,486, or those containing alkali metal salts of ethylpolyglycol ether phosphate esters together with sodium salts of condensation products of sulfonated phenols and formaldehyde according to European Pat. No. 22,925, are not stable to storage, either, in the case of the active substances cited above. Moreover, the suspension concentrates obtained with the above formulation auxiliaries are often insufficiently grindable in the pearl mills required for their manufacture, especially in the case of those formulations the viscosity of which depends on the temperature to a large extent. In those cases the suspensions often become viscous at temperatures from 35° to 55° C. which occur in the course of the grinding process.

It has now been found that a surprisingly large number of pesticides such as insecticides, acaricides, herbicides and fungicides can be formulated as liquid suspension concentrates stable to storage when using as formulation auxiliary a sulfosuccinic acid semiester, prepared from sodium sulfite, maleic anhydride and an alkylphenol polyglycol ether, together with a mixture of identical parts of salt of ligninsulfonic acid and a swelling alkaline earth metal silicate.

The subject of the invention is therefore liquid pesticidal compositions in the form of aqueous suspension concentrates, which in addition to the active substance or mixture of active substances contain an alkali metal salt of sulfosuccinic acid semiester prepared by reaction of a polyglycol ether of a condensation product of ($C_8$–$C_{12}$)-alkylphenol and formaldehyde with maleic anhydride and an alkali metal sulfite, and an alkali metal salt of a ligninsulfonic acid in admixture with identical parts of a swelling alkaline earth metal silicate.

The alkali metal salt of sulfosuccinic acid semiester to be used according to the invention is prepared according to German Pat. No. 2,132,405; in which process in particular monooctylphenols or monononylphenols are used, and the molar ratio alkylphenol:formaldehyde is varied between 2:1 and 10:9. The polyglycol ether of this condensation product of alkylphenol and formaldehyde preferably contains 2 to 8 mols of alkylene oxide moieties, especially ethylene oxide moieties, per mol of alkylphenol. Sodium sulfite is preferably used as an alkali metal sulfite.

By alkali metal salt of sulfosuccinic acid semiester there is to be understood especially the sodium salt.

A preferred sulfosuccinic acid semiester is, for example, prepared from 3 mols of nonylphenol, 18 mols of ethylene oxide, 2 mols of formaldehyde, 3 mols of sodium sulfite and 3 mols of maleic anhydride, and used in the form of a dry powder or an aqueous solution (generally 35% b.w.).

As an alkali metal salt of a ligninsulfonic acid, the sodium salt is used in particular. Suitable swelling alkaline earth metal silicates are especially calcium or magnesium silicates, preferably the mineral montmorillonite. A mixture of identical parts of sodium salt of ligninsulfonic acid and montmorillonite is commercially available under the trade name ®Davan No. 3 of the Vanderbilt Corporation.

Suitable active substances for the compositions of the invention are insecticides such as endosulfan, fungicides such as triphenyl tin compounds, especially fentin hydroxide, furthermore carbendazime, maneb or mancozeb, or herbicides such as those of the triazine type, preferably atrazine, simazine, or those of the urea derivative type such as diuron, linuron, monolinuron, monuron, isoproturon, chlorotoluron, especially diuron and chlorotoluron, or mixtures thereof.

Additionally, other usual formulation auxiliaries may be used in the compositions of the invention, for example normal wetting and dispersing agents such as polyoxethylated alkylphenols, polyoxethylated fatty alcohols, tridecyl alcohol polyglycol ether (®Genapol X-080), alkyl- or alkylphenylsulfonates, sodium salt of ligninsulfonic acid, sodium salt of 2,2'-dinaphthylmethane-6,6'-disulfonic, of dibutylnaphthalenesulfonic or of oleylmethyltauric acid, swelling agents such as swelling aluminosilicates or swelling polysaccharides, for example those prepared by fermentation of carbohydrates by means of Xanthomas microorganisms, such as ®Kelzan. Furthermore suitable as formulation auxiliaries are defoamers comprising tributylphosphate or a silicone such as dialkylpolysiloxanes, anti-freeze agents such as ethyleneglycol, propyleneglycol, and glycerol, especially ethyleneglycol, safeners such as urea, and the usual preservation agents such as benzoic acid, sorbitanoic acid, formaldehyde, traces of fungicidal substances etc.

For the preparation of the suspension concentrates of the invention, ordinary drinking water, processed water or deionized water may be used, preferably water having a (German hardness) degree of 20° dH.

The compositions of the invention can contain from 5 to 60, especially 15 to 50, weight percent of active substance(s), from 0.5 to 30, preferably 2 to 20, weight percent of the alkali metal salt of sulfosuccinic acid semiester, from 0.5 to 4 weight percent of a mixture of identical parts of an alkali metal salt of ligninsulfonic acid and a swelling alkaline earth metal silicate. As formulation auxiliaries, from 0 to 0.2 weight percent of a swelling polysaccharide, from 0 to 3.0 weight percent of usual wetting or dispersing agent, from 0 to 10 weight percent of anti-freeze agent, from 0 to 8 weight percent of safener, from 0 to 2 weight percent of preserving agent and from 0.2 to 3 weight percent of defoamer may be added further. The remainder to 100 weight percent of the composition of the invention consists of water.

The suspension concentrates of the invention are fluid and easily pourable. Surprisingly, their viscosity does not increase when the temperature rises up to 60° C.; the viscosity may even be decreased reversibly without adversely affecting the suspendibility and dilutability with water of the concentrates, which is important for storage and application in zones of hot climate. Products composed in accordance with the invention are easily grindable, they have a very good wettability and good dilutability on addition of water. They are furthermore excellently compatible and can be formulated into combinations of active substances, which are often applied in order to broaden the range of biological activity.

On the other hand, in the case where only one of the three formulation components of the invention is missing, that is, sulfosuccinic acid semiester, a salt of ligninsulfonic acid or a swelling alkaline earth metal silicate, the advantageous properties of the three-component combination according to the invention are completely lost, particularly the stability to storage, the pourability, and the viscosity behavior on rising storage temperatures. Likewise, the advantageous properties of the compositions according to the invention are lost in case the composition of the sulfosuccinic acid semiester is modified by omitting or adding one component, for example in case the sulfosuccinic acid semiester does not contain a polyglycol ether component.

For preparing, the suspension concentrates of the invention the active substance or mixture of active substances is, for example, stirred in an aqueous solution or a suspension of the formulation auxiliaries, the coarse-particle suspension obtained is optionally comminuted in a corundum disc mill or toothed disc mill to a fineness of about 200 microns, and, subsequently, the product is ground in a pearl mill or sand mill until the particles the suspension have a size of from 0.1 to 10 microns, preferably below 5 microns. The particle size is determined by means of a disc centrifuge or a Coulter Counter device.

The compositions of the invention are employed in simple manner by diluting the suspension concentrate with the intended amount of water, stirring the batch for a short time and applying it to the plant. The spray liquors obtained from the suspension concentrates of the invention, as compared to those prepared from wettable powders or emulsifiable concentrates, are distinguished especially by a homogeneous distribution of the active substance which is maintained even after 24 hours' standing. Contrary thereto, a suspension of wettable powder separates very rapidly; often, half of the active substance has already settled at the bottom after standing for ½ hour only. Likewise, emulsions precipitate the emulsified concentrates in oily or creamy form after 1 to 4 hours' standing.

Moreover, in the ready-for-use spray liquors, surprisingly the suspension concentrates of the invention have an excellent physical compatibility with known herbicidal, insecticidal and fungicidal products which may be added in the form of wettable powders or emulsifiable concentrates.

The following examples illustrate the invention.

EXAMPLES 1 TO 17

Flowable suspension concentrates of the following active substances having the following composition are prepared by grinding the components in a pearl mill provided with glass balls having a diameter of 2 mm. (see the following Table 1).

The dispersions are ground to such a fineness that 90 weight percent of the suspended particles have a diameter of less than 5 microns and 30 to 40 weight percent of the particles have a diameter of less than 1 micron, the particle size being measured by means of a disc centrifuge.

When 2 ml each of the suspension concentrates so obtained are poured into 99 ml of water, a suspension dilution forms spontaneously, in which traces only of sedimented particles are visible even after a 12 hours' standing. In contrast to comparable wettable powders, the suspendibility is nearly 100 percent in these cases (determined according to the CIPAC test prescriptions).

The dispersions obtained are easily pourable and remain stable even after a storage of three months with variation of the storage temperature between −10° C. to +50° C.

Sediment formation is not observed. Sometimes, part of the carrier liquid (from 5 to 10 percent by volume) only may separate, but by shaking twice, this part is spontaneously intermixed again with the other components. Crystal growth of the particles of active substance is not observed, either. The viscosity of the dispersion is not increased with rising storage temperature, on the contrary, its fluidity is increased without adversely affecting its stability.

TABLE 1

| Example No. | Weight % amount of components | | | | | | | | | | | | | | | | |
|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 | 17 |
| Endosulfan | 50 | 41 | 5 | — | — | — | — | — | — | — | — | — | — | — | — | — | — |
| Fentin hydroxide | — | — | — | 50 | 41.3 | 18.5 | — | — | — | — | — | — | — | — | — | — | — |
| Maneb | — | — | — | — | — | — | 30 | — | — | — | — | — | — | — | — | — | — |
| Mancozeb | — | — | — | — | — | — | — | 25 | — | — | — | — | — | — | — | — | — |
| Carbendazime | — | — | — | — | — | — | — | — | 30 | 20 | — | — | — | — | — | — | — |
| Diuron | — | — | — | — | — | — | — | — | — | — | 50 | 43 | — | — | — | — | — |
| Chlorotoluron | — | — | — | — | — | — | — | — | — | — | — | — | — | — | — | 50 | 41 |
| Atrazine | — | — | — | — | — | — | — | — | — | — | — | — | 45 | — | 22.5 | — | — |
| Simazine | — | — | — | — | — | — | — | — | — | — | — | — | — | 45 | 22.5 | — | — |
| Dispersing agent 1 (1+) | 7.5 | 5 | 2 | 5 | 4 | 4 | 20 | 21 | 50 | 1.85 | 4 | 4 | 3.5 | 3.5 | 3.5 | 7.5 | 5 |
| Dispersing agent 2 (2+) | 1.5 | 1 | 0.5 | 2 | 1 | 1 | 1 | 1.5 | 4 | 1 | 1 | 1 | 0.5 | 0.5 | 0.5 | 1.5 | 1 |
| Sodium oleyl-N-methyltauride | 0.5 | 0.5 | 1.0 | — | — | — | 1 | — | — | 0.5 | — | — | — | — | — | 0.5 | 0.5 |
| Tridecyl alcohol polyglycol ether | — | — | — | — | — | — | — | 2 | — | 2 | — | — | 0.5 | 1.5 | 1.5 | — | — |
| Polysaccharide (3+) | 0.2 | 0.2 | 0.1 | 0.1 | 0.1 | 0.2 | 0.1 | 0.1 | 0.1 | — | 0.1 | 0.1 | 0.1 | 0.1 | 0.1 | 0.2 | 0.2 |
| Defoamer (4+) | 2 | 2 | 3 | 2 | 2 | 2 | 2 | 2.4 | 2 | 3 | 1 | 1 | 3 | 3 | 3 | 2 | 2 |
| Urea | — | — | — | 6 | 6 | 12 | — | — | — | — | — | — | — | — | — | — | — |
| Ethyleneglycol | 8 | 8 | 10 | — | — | — | 5 | 7 | — | 10 | 8 | 8 | 8 | 8 | 8 | 8 | 8 |
| Preservation agent (5+) | 0.1 | 0.1 | — | 0.1 | 0.1 | 0.1 | — | — | — | — | 0.05 | 0.05 | 0.05 | 0.05 | 0.05 | 0.1 | 0.1 |
| Water | 30.2 | 42.2 | 78.4 | 34.8 | 45.5 | 62.2 | 40.9 | 41 | 13.9 | 61.65 | 35.85 | 42.85 | 39.35 | 38.35 | 38.35 | 30.2 | 42.2 |

(1+) Dispersing agent 1 Condensation product of 3 mols nonylphenol and 2 mols formaldehyde, oxethylated with 18 mols ethylene oxide reacted with 3 mols maleic anhydride and 3 mols sodium sulfite as 35% aqueous solution
(2+) Dispersing agent 2 Mixture of a Na salt of a ligninsulfonic acid with montmorillionite (identical parts) (®Darvan No. 3, Vanderbilt Corp. USA)
(3+) ®Kelzan, Kelce Corp., USA
(4+) Silicon defoamer SE 2 of Wacker Chemie GmbH
(5+) ®Bronidox L of Henkel AG

COMPARATIVE TEST I

When operating according to Examples 2, 5, 6, 9, 12 and 13 for the preparation of dispersions of the active substances of Table 1, while, however, replacing the dispersing agent 1 by a sulfo group-containing condensation product of an alkylphenol with formaldehyde, for example by ®Rapidamin Reserve D (that is, renouncing the polyglycol ether component), suspension concentrates are formed which become unstable after 1 month of storage at 50° C. already: jelly to viscous, partially solid sediments are formed which cannot be redispersed. These dispersions cannot be applied any more.

COMPARATIVE TEST II

When operating according to Examples 1, 2, 5, 6, 9, 12 and 13 for the preparation of dispersions of the active substances, while, however replacing the dispersing agent 2 by the sodium salt of a naphthalenesulfonic acid condensed with formaldehyde, for example ®Tamol NNO, or by sodium salt of ligninsulfonic acid alone, viscous sediments are formed on storage. The same effect is observed when using other known dispersing agents instead of the above condensation product of naphthalenesulfonic acid. These dispersions, too, cannot be used any longer.

What is claimed is:

1. A method for suspending a solid pesticide in water to form a concentrated aqueous suspension, said solid pesticide being selected from the group consisting of the herbicides diuron, chlorotoluron, simazine, or atrazine, the fungicides carbendazime, maneb, mancozeb, or fentin hydroxide, the insecticide endosulfan, and mixtures of said pesticides, which method comprises dispersing 15 to 50 percent, by weight of said suspension, of said solid pesticide or pesticides in water in the presence of 0.5 to 30 percent, by weight of said suspension, of an alkali metal salt of a sulfosuccinic acid semi-ester prepared by reaction of a polyglycol ether of a condensation product of a (C$_8$-C$_{12}$)-alkylphenol and formaldehyde with maleic anhydride and an alkali metal sulfite, and in the presence of 0.5 to 4 percent, by weight of said suspension, of a mixture of equal parts of an alkali metal salt of a ligninsulfonic acid and a swelling alkaline earth metal silicate.

2. A liquid pesticidal composition in the form of a concentrated aqueous suspension consisting essentially of 15 to 50 percent, by weight of said composition, of a solid pesticide selected from the group consisting of the herbicides diuron, chlorotoluron, simazine, or atrazine, the fungicides carbendazime, maneb, mancozeb, or fentin hydroxide, the insecticide endosulfan, and mixtures of said pesticides, which method comprises dispersing said solid pesticide or pesticides in water in the presence of 0.5 to 30 percent, by weight of said suspension, of an alkali metal salt of a sulfosuccinic acid semi-ester prepared by reaction of a polyglycol ether of a condensation product of a ($C_8$–$C_{12}$)-alkylphenol and formaldehyde with maleic anhydride and an alkali metal sulfite, and in the presence of 0.5 to 4 percent, by weight of said suspension, of a mixture of equal parts of an alkali metal salt of a ligninsulfonic acid and a swelling alkaline earth metal silicate, the balance of said composition being water.

3. A composition as in claim 2 wherein said pesticide is a herbicide.

4. A composition as in claim 2 wherein said pesticide is a fungicide.

5. A composition as in claim 2 wherein said pesticide is an insecticide.

6. A composition as in claim 2 wherein said polyglycol ether contains monooctylphenol or monononylphenol and formaldehyde in a molar ratio from 2:1 to 10:9 and from 2 to 8 mols of ethylene oxide moieties per mol of alkylphenol.

7. A composition as in claim 2 wherein said silicate is montmorillonite.

8. A composition as in claim 6 wherein said silicate is montmorillonite.

9. A composition as in claim 2 comprising carbendazime as a fungicide.

10. A composition as in claim 2 comprising fentin hydroxide as a fungicide.

11. A composition as in claim 2 additionally comprising 0 to 0.2 weight percent of a swelling polysaccharide, 0 to 3.0 weight percent of a wetting or dispersing agent, 0 to 10 weight percent of an anti-freeze agent, from 0 to 8 weight percent of a safener, 0 to 2 weight percent of a preservative, and 0.2 to 3 weight percent of a defoamer.

* * * * *